US008884779B2

(12) United States Patent
Herman et al.

(10) Patent No.: US 8,884,779 B2
(45) Date of Patent: Nov. 11, 2014

(54) EMI SHIELD FOR MEDICAL DEVICE TELEMETRY ANTENNA

(75) Inventors: Gerald M. Herman, Fridley, MN (US);
David R. Walsh, River Falls, WI (US);
Richard O. Berg, Maple Grove, MN (US); Lester O. Stener, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 705 days.

(21) Appl. No.: 13/168,297

(22) Filed: Jun. 24, 2011

(65) Prior Publication Data

US 2012/0326886 A1     Dec. 27, 2012

(51) Int. Cl.
*G08C 19/22*      (2006.01)
*A61N 1/378*      (2006.01)
*A61N 1/372*      (2006.01)
*H01F 38/14*      (2006.01)

(52) U.S. Cl.
CPC .......... *A61N 1/37229* (2013.01); *A61N 1/3787* (2013.01); *H01F 38/14* (2013.01); *Y10S 128/903* (2013.01)
USPC ................. 340/870.07; 340/572.7; 343/841; 607/32; 607/60; 128/903

(58) Field of Classification Search
USPC ............... 340/870.07, 572.7, 573.1; 343/841; 343/787, 715, 750; 607/32, 60; 128/901, 128/903
See application file for complete search history.

(56) References Cited

U.S. PATENT DOCUMENTS

| 5,527,348 | A | 6/1996 | Winkler et al. |
| 5,639,989 | A | 6/1997 | Higgins, III |
| 6,763,576 | B2 | 7/2004 | Watchko et al. |
| 7,493,167 | B2 * | 2/2009 | Hussein et al. ................. 607/36 |
| 8,160,705 | B2 * | 4/2012 | Stevenson et al. ............. 607/32 |
| 8,649,857 | B2 * | 2/2014 | Stevenson et al. .............. 607/2 |
| 2002/0032472 | A1 | 3/2002 | Zarinetchi et al. |
| 2005/0113888 | A1 | 5/2005 | Jimenez et al. |
| 2006/0217792 | A1 | 9/2006 | Hussein et al. |

FOREIGN PATENT DOCUMENTS

| WO | 00/02212 A1 | 1/2000 |
| WO | 2010/056751 A1 | 5/2010 |

OTHER PUBLICATIONS

International Search Report and Written Opinion of PCT/US2012/043564, dated Sep. 7, 2012, 10 pp.
International Preliminary Report on Patentability from international application No. PCT/US2012/043564, dated Jan. 9, 2014, 6 pp.
Spraylat Corporation, Technical Data Sheet, Series 599-B5085, Nickel Conductive Coating, http://www.cybershieldinc.com/, accessed Oct. 19, 2010, 2 pages.

* cited by examiner

*Primary Examiner* — Toan N Pham (57) ABSTRACT

A telemetry head for communication with an implantable medical device comprises a telemetry antenna and a shield substantially surrounding at least a portion of the antenna, the shield having a coating comprising a ferromagnetic material applied to at least a portion of the shield, wherein the coating is configured to shield at least the portion of the telemetry antenna from electromagnetic interference fields while permitting telemetry signals to pass through the coating.

32 Claims, 4 Drawing Sheets

EMI SHIELD FOR MEDICAL DEVICE TELEMETRY ANTENNA

TECHNICAL FIELD

The present disclosure relates to programmers for implantable medical devices, and in particular to telemetry heads for communicating with implantable medical devices.

BACKGROUND

Implantable medical devices (IMDs) are used to deliver therapy to patients for the treatment of a variety of symptoms or conditions. Examples include implantable stimulators, such as an implantable neurostimulator, a cardiac pacemaker, an implantable cardioverter-defibrillator (ICD), and implantable fluid delivery devices. Each IMD typically delivers therapy according to a number of programmable parameters. For example, for a neurostimulator, a clinician may select a pulse amplitude, which may be a current or voltage amplitude, a pulse width, a pulse rate, a pulse profile (e.g., number of pulses per burst and the number of bursts over a period of time), the electrode or electrodes from which pulses may be delivered, as well as the polarities of the electrodes. An IMD may also be configured to store data about a patient's condition and the treatment delivered to the patient, which a clinician may wish to retrieve for analysis.

A clinician may use an external computing device, generally referred to as a programmer, to program parameters that are sent to the IMD or to receive and view data that is retrieved from the RID. The external computing device may be electrically coupled to an antenna device, sometimes referred to as a telemetry head, which converts the programmed parameters into wireless telemetry signals, such as radio frequency (RF) telemetry, signals, that are received by a corresponding telemetry antenna of the IMD. The telemetry head may also receive telemetry signals from the IMD that correspond to patient or treatment data, which is converted by the telemetry head into data usable by the external programmer.

SUMMARY

In general, the present disclosure is directed to a telemetry head for communicating with an implantable medical device comprising a shield within a main housing of the telemetry head for shielding at least a portion of a telemetry antenna from electromagnetic interference (EMI). A coating comprising a ferromagnetic shielding material is applied to at least a portion of the shield, wherein the coating is configured to permit passage of telemetry signals, such as inductive (magnetic field) telemetry signals, while shielding at least a portion of the antenna from EMI such as electrical fields.

In one example, the present description is directed to a telemetry head, such as a telemetry head for use with an implantable medical device programmer, wherein the telemetry head comprises a telemetry antenna and a shield substantially surrounding at least a portion of the antenna, the shield having a coating comprising a ferromagnetic material applied to at least a portion of the shield, wherein the coating is configured to shield at least the portion of the telemetry antenna from electromagnetic interference fields while permitting telemetry signals to pass through the coating.

In another example, the present disclosure is directed to a programmer for a medical device, the programmer comprising a telemetry antenna, a shield substantially surrounding at least a portion of the antenna, the shield having a coating comprising a ferromagnetic material applied to at least a portion of the shield, wherein the coating is configured to shield at least the portion of the telemetry antenna from electromagnetic interference fields while permitting telemetry signals to pass through the coating, and programmer electronics electrically coupled to the telemetry antenna, wherein the programmer electronics are configured to transmit and receive telemetry signals via the telemetry antenna.

In another example, the present disclosure is directed to a system comprising an implantable medical device, a telemetry head configured to communicate with the implantable medical device via telemetry signals, the telemetry head comprising a telemetry antenna and a shield substantially surrounding at least a portion of the antenna, the shield having a coating comprising a ferromagnetic material applied to at least a portion of the shield, wherein the coating is configured to shield at least the portion of the telemetry antenna from electromagnetic interference fields while permitting telemetry signals to pass through the coating, and a programmer electrically coupled to the telemetry head, the programmer comprising programmer electronics configured to transmit telemetry signals to the implantable medical device and to receive telemetry signals from the implantable medical device via the telemetry antenna.

In another example, the present disclosure is directed to a method comprising applying a coating comprising a ferromagnetic material to at least a portion of a shield, placing the shield around at least a portion of a telemetry antenna so that the coating substantially surrounds at least the portion of the telemetry antenna, wherein the coating is configured to shield at least the portion of the telemetry antenna from electromagnetic interference fields while permitting telemetry signals to pass through the coating, and placing the telemetry antenna and the shield within an exterior housing.

In another example, the present disclosure is directed to a telemetry head for communication with an implantable medical device, the telemetry head comprising means for transmitting telemetry signals to an implantable medical device or for receiving telemetry signals from the implantable medical device, means for shielding the means for transmitting telemetry signals or receiving telemetry signals, the means for shielding substantially, surrounding at least a portion of the means for transmitting telemetry signals or receiving telemetry signals, and means for coating at least a portion of the means for shielding, the means for coating comprising a ferromagnetic material, wherein the means for coating is configured to shield at least the portion of the means for transmitting telemetry signals or receiving telemetry signals from electromagnetic interference fields while permitting telemetry signals to pass through the means for coating.

The details of one or more examples of the disclosure are set forth in the accompanying drawings and the description below. Other features, objects, and advantages of the disclosure will be apparent from the description, the drawings, and from the claims.

DETAILED DESCRIPTION

In general, the present disclosure is directed to a telemetry head for communicating with and/or programming an implantable medical device (IMD). The telemetry head comprising a shield within a main housing of the telemetry head for shielding at least a portion of a telemetry antenna from electromagnetic interference (EMI). In some examples, telemetry signals are transmitted by inductive (magnetic field) telemetry and the telemetry antenna comprises an inductive (magnetic) coil for transmitting or receiving inductive (magnetic field) telemetry signals. A coating comprising a ferromagnetic material is applied to at least a portion of the shield, wherein the coating is configured to permit the passage of telemetry signals, such as magnetic-field telemetry signals, while shielding at least a portion of the antenna from EMI, such as electrical-field interference. In one example, the conductivity of the coating is such that the coating is marginally conductive to allow for the shielding of electric fields, e.g., to prevent or reduce eddy current losses, but not so conductive that the coating interferes with the passage of magnetic-field telemetry signals through the shield.

Figure 1:
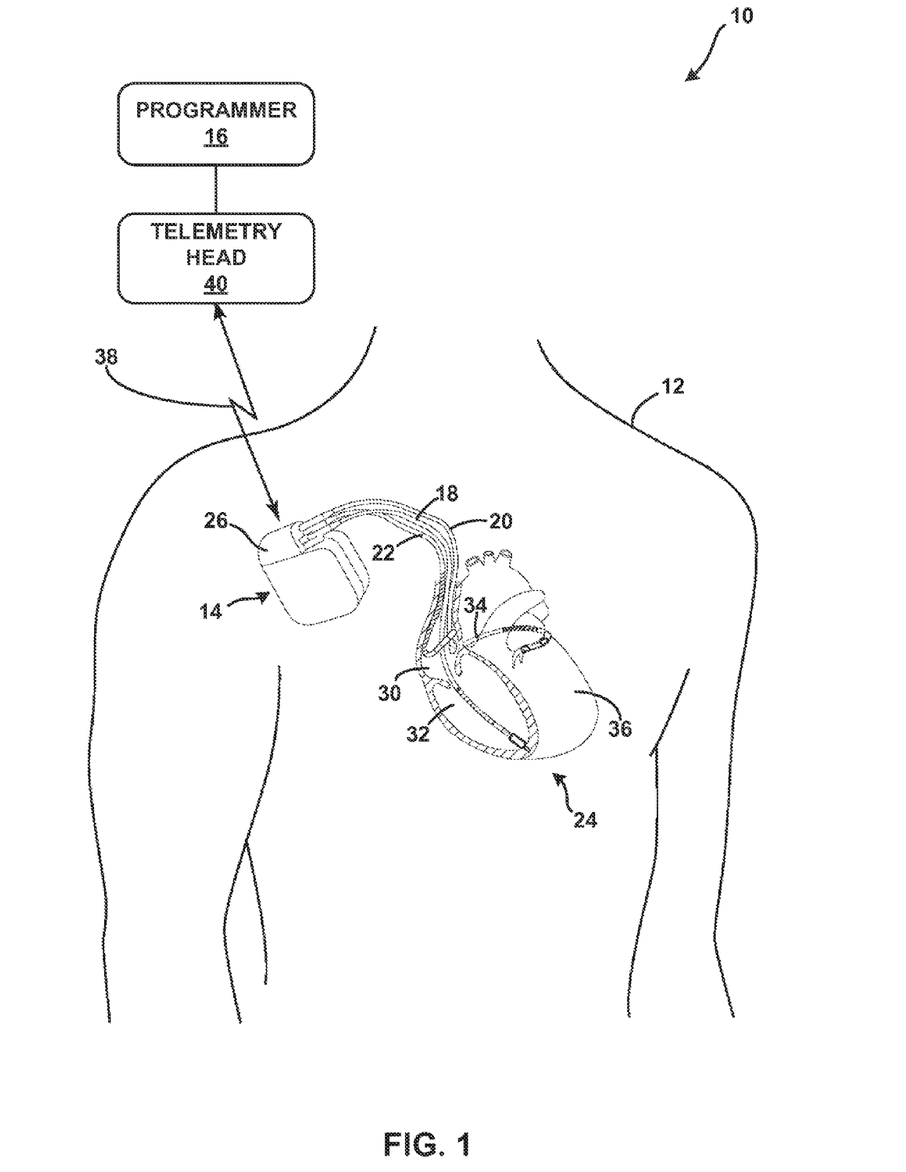
FIG. 1 is a conceptual diagram illustrating an example therapy system comprising an implantable medical device that may be used to monitor one or more physiological parameters of a patient and/or provide therapy to the patient and a programmer system comprising a programmer and a telemetry head.

FIG. 1 is a conceptual diagram illustrating an example therapy system 10 that may be used to provide therapy to a patient 12. Patient 12 ordinarily, but not necessarily, will be a human. Therapy system 10 may include an implantable medical device (IMD) 114, such as an implantable cardiac device, and a programmer 16. In the example depicted in FIG. 1, IMD 14 is connected (or "coupled") to leads 18, 20, and 22 via a connector block 26. IMD 14 may be, for example, a device that provides cardiac rhythm management therapy, and may include, for example, an implantable pacemaker, cardioverter, and/or defibrillator that provides therapy to heart 24 of patient 12 via electrodes coupled to one or more of leads 18, 20, and 22. In some examples, IMD 14 may deliver pacing pulses, but not cardioversion or defibrillation shocks, while in other examples, IMD 14 may deliver cardioversion or defibrillation shocks, but not pacing pulses. In addition, in further examples, IMD 14 may deliver pacing pulses, cardioversion shocks, and defibrillation shocks.

Leads 18, 20, 22 that are coupled to IMD 14 may extend into the heart 24 of patient 12 to sense electrical activity of heart 24 and/or deliver electrical stimulation to heart 24. In the example shown in FIG. 1, right ventricular lead 18 extends through one or more veins (not shown), the superior vena cava (not shown), and right atrium 30, and into right ventricle 32. Left ventricular coronary sinus lead 20 extends through one or more veins, the vena cava, right atrium 30, and into the coronary sinus 34 to a region adjacent to the free wall of left ventricle 36 of heart 24. Right atrial lead 22 extends through one or more veins and the vena cava, and into the right atrium 30 of heart 24. In some examples, IMD 14 may deliver stimulation therapy to heart 24 by delivering stimulation to an extravascular tissue site in addition to or instead of delivering stimulation via electrodes of intravascular leads 18, 20, 22.

IMD 14 may sense electrical signals attendant to the depolarization and repolarization of heart 24 (e.g., cardiac signals) via electrodes coupled to at least one of the leads 18, 20, 22 (not shown). In some examples, IMD 14 provides pacing pulses to heart 24 based on the cardiac signals sensed within heart 24. The configurations of electrodes used by IMD 14 for sensing and pacing may be unipolar or bipolar. IMD 14 may also provide defibrillation therapy and/or cardioversion therapy via electrodes located on at least one of the leads 18, 20, 22. IMD 14 may detect arrhythmia of heart 24, such as fibrillation of ventricles 32 and 36, and deliver defibrillation therapy to heart 24 in the form of electrical shocks. In some examples, IMD 14 may be programmed to deliver a progression of therapies, e.g., shocks with increasing energy levels, until a fibrillation of heart 24 is stopped. IMD 14 may detect fibrillation by employing one or more fibrillation detection techniques known in the art. For example, IMD 14 may identify cardiac parameters of the cardiac: signal, e.g., R-waves, and detect fibrillation based on the identified cardiac parameters.

In some examples, programmer 16 may be a handheld computing device or a computer workstation. Programmer 16 may include a user interface that receives input from a user. The user interface may include, for example, a keypad and a display, which may be, for example, a cathode ray tube (cRT) display, a liquid crystal display (LCD) or light emitting diode (LED) display. The keypad may take the form of an alphanumeric keypad or a reduced set of keys associated with particular functions. Programmer 116 can additionally or alternatively include a peripheral pointing device, such as a mouse, via which a user may interact with the user interface. In some examples, a display of programmer 16 may include a touch screen display, and a user may interact with programmer 16 via the display.

A user, such as a physician, technician, or other clinician, or patient 12 may interact with programmer 16 to communicate with IMD 14. For example, the user may interact with programmer 16 to retrieve physiological or diagnostic information from IMD 14, A user may also interact with programmer 16 to program IMD 14, e.g., select values for operational parameters of IMD 14.

Programmer 16 may communicate with IMD 14 via a wireless communication link 38, such as via low frequency or radio frequency (RF) telemetry, but other techniques are also contemplated. In one example, wireless communication link comprises inductive telemetry, such as near-field telemetry via magnetic fields. Programmer 16 may be coupled to a telemetry head 40 that may be placed proximate to the patient's body near the IMD 14 implant site in order to improve the quality or security of communication between IMD 14 and programmer 16. As described in more detail below, telemetry head 40 comprises an antenna for transmitting telemetry signals to IMD 14 and receiving telemetry signals from IMD 14. Programmer 16 may be directly coupled to telemetry head 40, e.g., via a cable or other electrical connection, or programmer 16 may communicate with telemetry head 40 via another wireless communication link.

Although IMD 14 has been described as an implantable cardioverter-defibrillator, other IMDs may be used to implement certain techniques of this disclosure. For example, telemetry head 40 may be configured to communicate via a wireless communication link 38 with an implantable neurostimulator capable of treating symptoms or conditions such as chronic pain, tremor, Parkinson's disease, epilepsy, incontinence, or gastroparesis. Telemetry head 40 may also be configured to communicate with an implantable fluid delivery device for the delivery of therapeutic agents, such as drugs, insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics to treat, manage or otherwise control various conditions or disorders of patient 12, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, and mood disorders. Telemetry head 40 may be used with other implantable devices where communication between the implantable device and an exterior device, such as a programmer 16, is desired.

Figure 2:
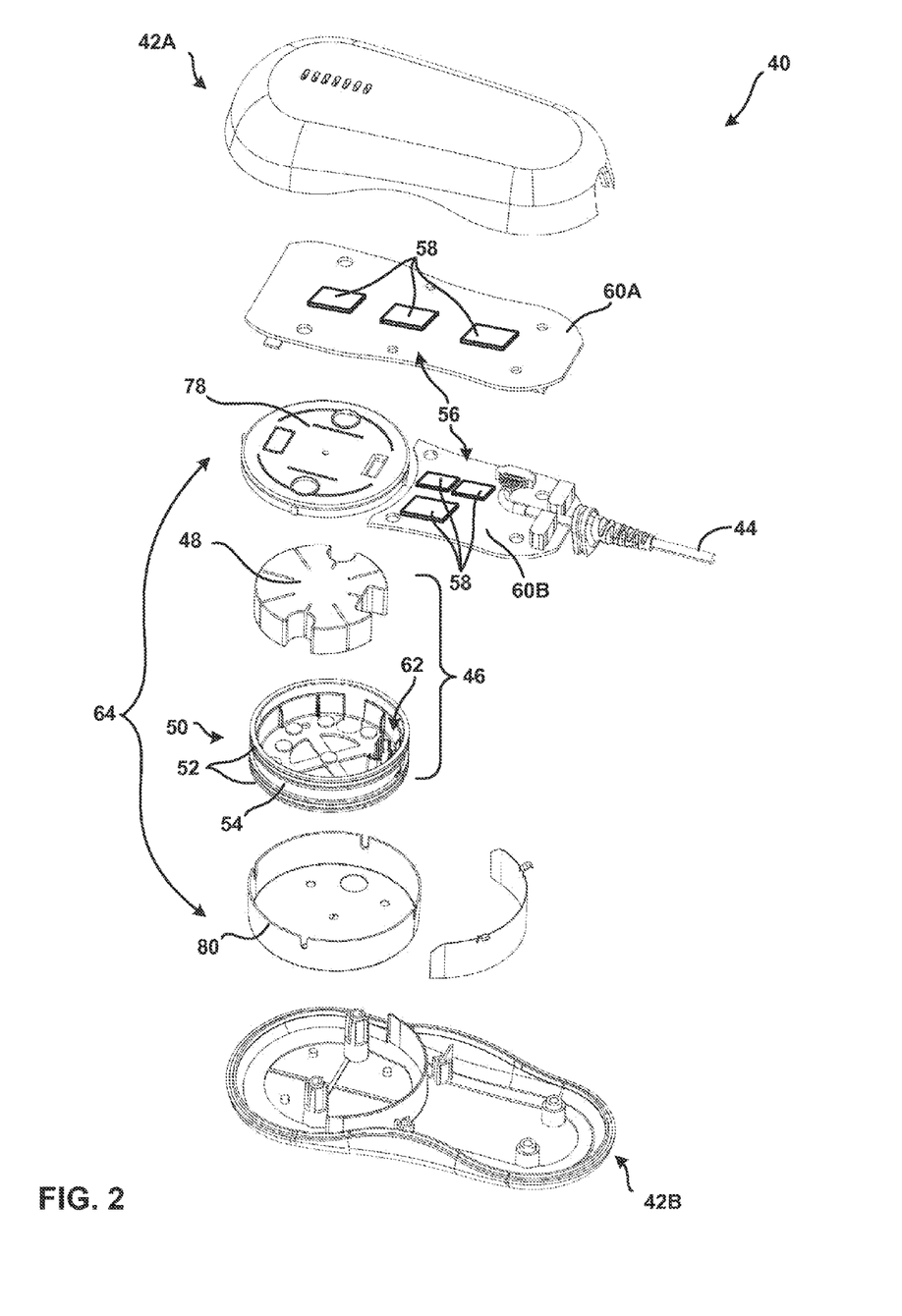
FIG. 2 is an exploded perspective view illustrating an example telemetry head for communicating with an implantable medical device.

FIG. 2 is an exploded perspective view of an example telemetry head 40 that may be used with system 10. Telemetry head 40 may include a main housing 42, which may be formed by an upper housing 42A and a lower housing 42B. Telemetry head 40 may be connected to an external computing device, such as programmer 16, via a cable 44 or other means of transmitting signals between telemetry head 40 and programmer 16. Telemetry head 40 further comprises a telemetry antenna 46 that performs at least one of transmitting telemetry signals to a device, such as IMD 14, or receives telemetry signals from the device, such as via wireless communications link 38. In one example, telemetry antenna 46 is an inductive (magnetic) antenna for transmitting and/or receiving telemetry signals via magnetic fields, such as through inductive coupling with a corresponding inductive telemetry antenna within IMD 14. Inductive antenna 46 may comprise a magnetic core 48 surrounded by a coil 50 comprising one or more turns of a conductor 52, wherein magnetic core 48 is configured to transmit and/or receive inductive (magnetic field) signals. In the example shown in FIG. 2, coil 50 is carried on a bobbin 54 that surrounds magnetic core 48. One or more conductors 52 are arranged on bobbin 54, such as on an outer surface of bobbin 54. Telemetry antenna 46 may transmit inductive telemetry signals by passing a current through coil 50 which causes magnetic core 48 to produce a magnetic field that is transmitted to IMD 14. Telemetry antenna 46 may receive inductive telemetry signals via magnetic core 48, which results in an induced current through coil 50.

System 10 may further comprise electronics 56 for producing and transmitting telemetry signals and/or for receiving and interpreting telemetry signals. In one example, shown in FIG. 2, electronics 56 are included within telemetry housing 42, such as via one or more electronics components 58 mounted on one or more wiring boards 60A, 60B that are configured to generate electrical signals that are transmitted as telemetry signals by telemetry antenna 46 and/or to receive and interpret electrical signals corresponding to telemetry signals received by telemetry antenna 46. In one example, the telemetry signals generated by electronics 56 and transmitted by telemetry antenna 46 may comprise telemetry signals transmitted to an implantable medical device, such as programming instructions for programming IMD 14 and/or telemetry signals received from an implantable medical device, such as data relating to patient 12 being treated by IMD 14 or data relating to the treatment provided by IMD 14 to patient 12.

Electronics 56 for the generation or interpretation of telemetry signals may be included in another device, such as an external computing device, for example programmer 16. In such a case, electronics components 58 within telemetry housing 42 may be omitted, or electronics components 58 may serve another purpose (such as filtering, amplifying, or transmitting the electrical signals corresponding to telemetry signals). In one example, electronics 56 comprise radio frequency (RF) electronics electrically coupled to antenna 46 are configured to generate RE signals for transmission via antenna 46 and/or RF electronics electrically coupled to antenna 46 that are configured to receive RF signals from antenna 46. In such an example, antenna 46 is an RF antenna having a structure configured to transmit and/or receive RF signals, such as inductive (magnetic field) telemetry signals at a radio frequency.

Telemetry antenna 46 may be electrically coupled to cable 44 to provide for the transmission of electrical signals corresponding to telemetry signals between telemetry antenna 46 and an external device, such as programmer 16. In one example, coil 50 of telemetry antenna 46 is electrically coupled to cable 44 through a plurality of connection pins 62 that extend up from bobbin 54 past magnetic core 48 and are electrically coupled to wiring board 60A (see FIG. 5). Traces or other conductors (not shown) transmit the electrical signals to cable 44, such as via wiring boards 60A and 60B. Other electrical connection arrangements are possible. If electronics 56 for producing and transmitting telemetry signals and/or receiving and interpreting telemetry signals are included within telemetry head 40, then the traces or conductors on wiring boards 60A, 60B may carry the electrical signals to or from electronics components 58.

As shown in the example of FIG. 2, telemetry head 40 may be coupled to an external computing device, such as programmer 16, via cable 44 so that electrical signals may be transmitted between telemetry head 40 and the external computing device. In some examples, however, telemetry head 40 may be communicatively coupled to the programmer 16 by other means, such as via a wireless communication link, for example a WiFi or Bluetooth connection. Telemetry head 40 may also be coupled to another external computing device, such as a personal computer or a computer network, wherein the other external computing device communicates with programmer 16.

Telemetry head 40 also comprises a shield 64 surrounding at least a portion of telemetry antenna 46, wherein shield 64 provides for shielding against electromagnetic interference (EMI) noise that could be picked up by antenna 46 and interfere with telemetry operations of telemetry head 40. In one example, shield 64 comprises a polymeric material, such as a thermoplastic acrylonitrile butadiene styrene (ABS), polycarbonate (PC), or an ABS-PC blend). A coating 66 is applied to at least a portion of a surface of shield 64 (see FIGS. 4 and 5), wherein coating 66 comprises a ferromagnetic material that is configured to allow telemetry signals to pass through coating 66 while preventing EMI from passing through coating 66. In one example, coating 66 substantially surrounds at least a portion of antenna 46 to allow telemetry signals to pass while shielding EMI away from the portion of antenna 46. In one example, wherein telemetry, head 40 communicates via inductive (magnetic) telemetry, e.g. via magnetic fields, and telemetry antenna 46 comprises an inductive antenna, such as the example antenna 46 comprising magnetic core 48 and coil 50, described above, coating 66 is configured to allow magnetic fields, such as those corresponding to telemetry signals from inductive antenna 46, while shielding electrical fields from antenna 46.

Coating 66 is electrically conductive so that EMI, such as electrical fields, that encounter shield 64 and coating 66 will be conducted along coating 66 away from telemetry antenna 46. In one example, coating 66 has an overall resistivity that is sufficiently low (e.g., a conductivity that is sufficiently high) to provide for the conduction of electrical current away from antenna 46, but not with a resistivity so low (e.g., a conductivity so high) as to interfere with the passage of telemetry signals, such as inductive telemetry signals, through coating 66 and shield 64. In one example, coating 66 may have a resistivity of between about 0.1 ohms per $cm^2$ and about 1 ohm per $cm^2$, for example, between about 0.2 ohms per $cm^2$ and about 0.5 ohms per $cm^2$.

In one example, the ferromagnetic material of coating comprises nickel. In other examples, the ferromagnetic material comprises iron. In other examples, the ferromagnetic material may comprise combinations of ferromagnetic materials, such as nickel in combination with iron. In one example, coating 66 comprises a conductive paint that may be coated onto shield 64, such as via spraying, dipping, or other liquid coating techniques. In other examples, the ferromagnetic material may be deposited via other deposition techniques, such as via sputtering or vapor deposition. In one example, vacuum deposition may be used to deposite a copper-based adhesion coating followed by a top coat including one or more of nickel, silver, or stainless steel. In one example, coating 66 comprises a nickel-containing paint comprising nickel solids, such as a nickel powder, suspended in a paint, wherein the weight percentage of nickel in the paint is selected to provide a desired resistivity of coating 66. In one example, a paint that may be used for coating may comprise between about 20 weight % nickel solids and about 50 weight % nickel solids. Examples of paints or coatings that may be used to form coating 66 include conductive paints sold by Spraylat Corporation (Mt. Vernon, N.Y.), such as the Spraylat Series 599-B5085 nickel conductive coating paint, coatings sold under the ELECTRODAG trade name by Achenson Colloids Co. (Port Huron, Mich.), such as ELECTRODAG 550 nickel coating, coatings sold under the ISOLEX trade name by Randolph Products Co. (Chicopee, Mass.), such as ISOLEX WP-120 waterborne nickel coating or ISOLEX R65 nickel acrylic.

Figure 3:
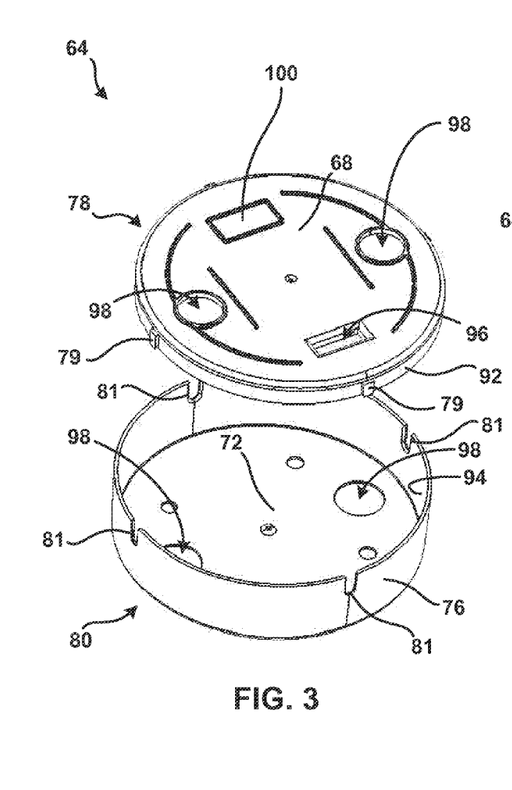
FIG. 3 is an exploded perspective view of a shield for shielding a telemetry antenna of the telemetry head from electromagnetic interference (EMI).
Figure 4:
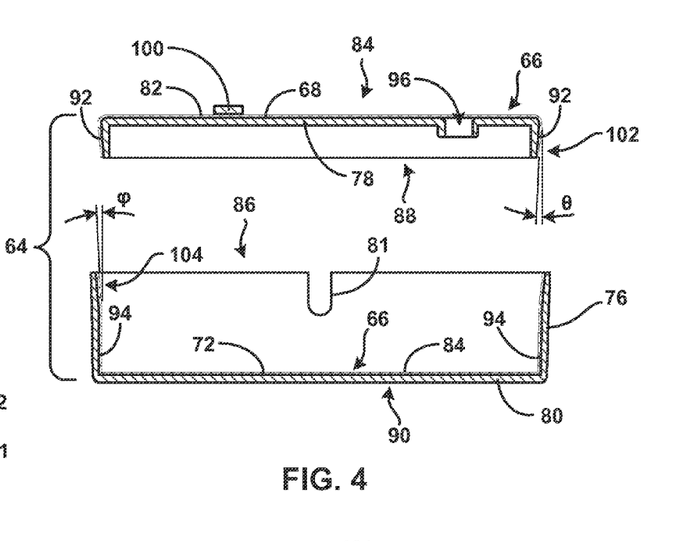
FIG. 4 is an exploded lateral cross-sectional view of the shield of FIG. 3.
Figure 5:
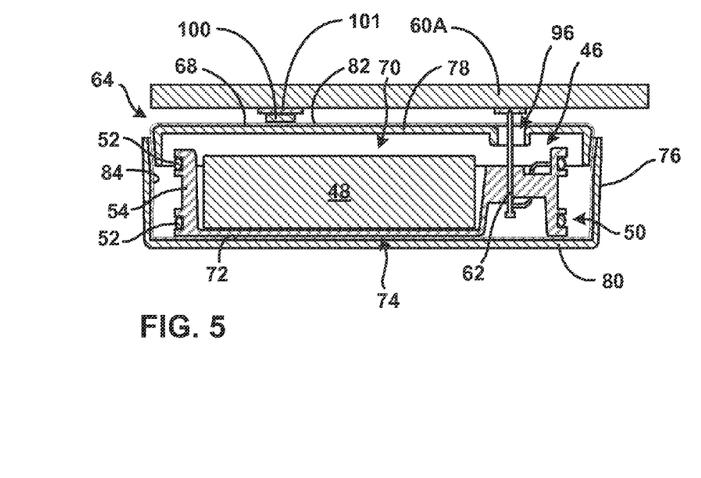
FIG. 5 is a lateral cross-sectional view of the shield of FIGS. 4 and 5 surrounding a telemetry antenna, wherein the telemetry antenna is electrically coupled to a wiring board.

In one example, shielding coating 66 is applied to at least a portion of a first major surface 68 of shield 64 located on a first side 70 of telemetry antenna 46 and to at least a portion of a second major surface 72 located on a second side 74 of telemetry antenna 46 (FIG. 5). The term "major surface" of shield 64 as it is used herein refers to a surface having a relatively larger surface area compared to other minor surfaces of shield 64, such as side surface 76. As shown in the example of FIGS. 3-5, major surfaces 68, 70 have a surface area that is substantially larger than a surface area of a minor surface such as side surface 76. In one example, shown in FIGS. 4 and 5, coating 66 substantially covers the entirety of first major surface 68 and substantially covers the entirety of second major surface 72.

In one example, shield 64 comprises an upper shield 78 and a lower shield 80 that are mechanically coupled together to form shield 64. In such a configuration, coating 66 may comprise an upper coating 82 applied to upper shield 78 and a tower coating 84 applied to lower shield 80 (FIGS. 4 and 5). Upper shield 78 and lower shield 80 may comprise orienting structures to ensure a desired orientation between upper shield 78 and lower shield 80. In the example shown in FIG. 3, upper shield 78 comprises a plurality of tabs 79, wherein each tab 79 is received by a corresponding groove 81 within lower shield 80. Tabs 79 and grooves 81 ensure that upper shield 78 and lower shield 80 are properly oriented, e.g. radially oriented, before mechanically coupling upper shield 78 and lower shield 80, and to prevent shields 78, 80 from rotating with respect to each other. Other orienting structures may be used, such as one or more tabs in tower shield 80 that are received by corresponding grooves in upper shield 78, or a detent mechanism between shields 78, 80, such as a ball bearing that is biased into a depression.

In one example, shown best in FIG. 4, upper coating 82 substantially covers an entire side of upper shield 78, such as a top side 84 of upper shield, while lower coating substantially covers an entire side of lower shield 80, such as a top side 86 of lower shield 80. Alternatively, upper coating 82 may substantially cover a bottom side 88 of upper shield 78. Similarly, tower coating 84 may substantially cover a bottom side 90 of lower shield 80. In one example, shown best in FIG. 4, upper coating 82 substantially covers a top major surface 68 as well as outer side surfaces 92, while lower coating 84 substantially covers atop major surface 72 as well as inner side surfaces 94.

Coating 66 is electrically grounded so that electrical current that results in coating 66 from EMI will be conducted along coating 66 and away from telemetry antenna 46 so that the EMI current will not interfere with telemetry signals passing through shield 64. Coating 66 may be grounded by several means. In one example, a conductive pad 100 is electrically coupled to coating 66 and is electrically coupled to a ground, such as a ground terminal on wiring board 60A, for example, via a contact pad 101 (FIG. 5). Conductive pad 100 may comprise a conductive tape, such as a conductive foam tape, which comprises an electrically conductive material embedded and a pressure sensitive adhesive (PSA). In one example, the conductive material of conductive pad 100 may comprise conductive fibers (such as, e.g., one or more of silver fibers, nickel fibers, copper fibers, gold fibers, and the like) loaded as a dispersion within a urethane foam matrix that is backed with a conductive acrylic PSA. Suitable conductive acrylics may include those commercially available from 3M of St. Paul, Minn. The direct contact between conductive pad 100 and coating 66 and between conductive pad 100 and to wiring board 60A provides a conductive pathway between coating 66 and the ground of wiring board 90A.

Other methods of grounding coating 66 may be used, such as bonding a conductor, such as a wire, to coating 66 and to aground, metal stampings, such as a leaf spring or compression spring that is placed between coating 66 and a ground, an elastomer loaded with conductive particles, such as nickel, that is placed between coating 66 and a ground, EMI gasketing, such as a foil over a foam or a metalized fabric over a foam, or direct clamping of coating 66 to a ground, such as by mounting shield 64, e.g., one or both of upper shield 78 and lower shield 80, to a wiring board 60A or 60B. In some examples, one or more conductive gaskets and/or seals (e.g., those commercially available from Chromerics of Woburn, Mass.) may be used to ground coating 66.

In one example, wherein coating 66 comprises an upper coating 82 on upper shield 78 and a lower coating 84 on lower shield 80, each coating 82, 84 may have its own electrical connection to a ground, such as a first conductive pad 100 mounted on upper coating 82 and a second conductive pad (not shown) mounted on lower coating 84, wherein each conductive pad is electrically connected to aground. Alternatively, a common electrical connection may be used to electrically couple both upper coating 82 and lower coating 84 to a ground. In the example shown in FIGS. 4 and 5, upper coating 82 is directly electrically coupled to a ground (e.g., wiring board 60A) via conductive pad 100, and lower coating 84 is electrically coupled to upper coating 82. Many methods may be used to electrically couple lower coating 84 to upper coating 82, such as bonding one or more conductors, such as wires, so that each conductor is electrically coupled to lower coating 84 at one end and to upper coating 82 an another end. In one example, described in more detail below, lower coating 84 is electrically coupled to upper coating 82 via a direct physical connection between upper coating 82 and lower coating 84, such as via an interference fit between upper shield 78 and lower shield 80, described in more detail below.

Upper shield 78 and lower shield 80 may be configured such that when shields 78, 80 are mechanically coupled together, upper coating 82 is electrically coupled to lower coating 84 without additional structures being required. In one example, upper shield 78 is mechanically coupled to lower shield 80 such that upper coating 82 is in contact with lower coating 84 to provide an electrical coupling between coatings 82, 84. In the example shown in FIGS. 3-5, an interference fit is formed between upper shield 78 and lower shield 80, e.g., so that one shield 78, 80 is frictionally held by the other. In one example, best shown in FIG. 4, upper shield 78 comprises a taper 102 and lower shield 80 comprises a corresponding mating taper 104. In one example, taper 102 of upper shield 78 is formed at a lower portion of outer side surfaces 92 of upper shield 78 and taper 104 of tower shield 80 is formed at an upper portion of inner side surfaces 94 of tower shield 80. Although FIGS. 4 and 5 show taper 102 formed on an outer surface 92 of upper shield 78 and taper 104 formed on an inner surface 94 of lower shield 80, the tapers could be reversed, e.g., with a taper formed on an inner surface of upper shield 78 and a corresponding mating taper formed on an outer surface of lower shield 80.

Taper 102 forms a taper angle θ with respect to an axial direction of upper shield 78 and taper 104 forms a corresponding taper angle φ with respect to an axial direction of lower shield 80. In one example, taper angles θ, φ are substantially equal to each other. In one example, each taper angle θ, φ is between about 1 degree and about 3 degrees, for example, between about 1.5 degrees and about 2.5 degrees, such as between about 1.9 degrees and about 2.1 degrees, for example about 2 degrees. In one example, it has been found that a 2-degree taper for taper angles θ, φ provides sufficient radial force between upper shield 78 and tower shield 80 over time, as discussed below, to provide sufficient electrical contact between upper coating 82 and lower coating 84 throughout a desired life of telemetry head 40.

In one example, tapers 102 and 104 are configured to provide sufficient radial pressure, also referred to as "hoop" pressure, between upper coating 82 and lower coating 84 so that an electrical connection is formed between upper coating and tower coating. In one example, tapers 102, 104 are configured so that an operator assembling shield 64 from upper shield 78 and lower shield 80 can provide sufficient axial force between upper shield 78 and lower shield 80 to engage tapers 102, 104 and form an interference fit without the need to use a machine for assembly.

In some examples, wherein upper shield 78 and lower shield 80 are made from a thermoplastic elastomeric material or another material that may relax over time, such that the hoop pressure between upper coating 82 and lower coating 84 may diminish over time. In one example, tapers 102 and 104 may also be configured to accommodate for a relaxing of hoop pressure that may occur over time due to a relaxing of the material of shields 78, 80. For example, taper angles θ, φ may be selected to provide a larger hoop pressure than is necessary for electrical connection between upper coating 82 and lower coating 84 so that as the material of shields 78, 80 relaxes over time, the pressure is still sufficient to provide for electrical coupling between upper coating 82 and lower coating 84.

In one example, upper coating 82 is formed around substantially an entire edge of upper shield 78, e.g., around substantially the entire circumference of a generally circular or generally elliptical upper shield 78, and tower coating 84 is formed around substantially an entire edge of lower shield 78, e.g., around substantially the entire circumference of a generally circular or generally elliptical lower shield 80. In such examples, taper 102 may also be formed around substantially the entire edge of upper shield 78 and taper 104 may be formed around substantially the entire edge of lower shield 80. In one example, shown in FIGS. 4 and 5, upper coating 82 is applied around substantially the entire outer circumference of outer surface 92 and lower coating 84 is applied around substantially the entire inner circumference of inner surface 94. In such examples, taper 102 may be formed around substantially the entire outer circumference of outer surface 92 of upper shield 78 and taper 104 may be formed around substantially the entire inner circumference of inner surface 94 of lower shield 80.

When tapers 102, 104 are formed around substantially the entire edge of shields 78, 80, respectively, and coatings 82, 84 are applied around substantially the entire edge of shields 78, 80, respectively, upper coating 82 may be electrically coupled to lower coating 84 around substantially the entire edge. Electrically coupling upper coating 82 to lower coating 84 around substantially the entire edge, e.g., substantially around the entire circumference of generally circular or generally shields 78, 80, provides for better conduction of EMI-generated current in coating 66 away from telemetry antenna 46 because the EMI-generated current can take the shortest path to the grounding structure, such as conductive pad 100. Electrical coupling around substantially the entire edge of coatings 82, 84 may also provide for more reliable shielding because it provides for redundancy of the electrical connection between upper coating 82 and lower coating 84.

It has been found that a taper angle θ, φ of between about 1 degree and about 3 degrees, for example, between about 1.5 degrees and about 2.5 degrees, such as between about 1.9 degrees and about 2.1 degrees, for example about 2 degrees, provides a balance between ease of assembly and sufficient hoop pressure to provide for electrical connection around substantially the entire circumference of upper coating 82 and lower coating 84 as well as sufficient hoop pressure to accommodate relaxation of the material of shields 78, 80.

In the example shown in FIGS. 4 and 5, coating 66, such as the coating 66 formed by upper coating 82 and lower coating 84 substantially surrounds at least a portion of telemetry antenna 46. For example, as shown best in FIG. 5, upper coating 82 and lower coating 84 substantially surround all of coil 50 and magnetic core 48 to provide a substantially continuous shield 66 around telemetry antenna 46. In the example shown in FIGS. 4 and 5, the only portions of antenna 46 that are not surrounded by coating 66 are an opening through which an electrical connection may be made between antenna 46 and electronics 56, such as opening 96 through which connection pins 62 may extend, and openings through which attachment structures may be inserted, such as openings 98 (FIG. 3) that accommodate screws or other fasteners (not shown) for connecting telemetry head 40 together.

The use of an interior shield 64 with a coating 66 that substantially surrounds at least a portion of telemetry antenna 46 has several advantages over applying a shielding coating to the main housing 42 of telemetry head 40. For example, because interior shield 64 is smaller than main housing 42, applying coating 66 to the interior shield 64 is less expensive than applying a similar coating to main housing 42 because less of the coating material is necessary.

In some examples, applying a coating 66 to interior shield 64 may be easier and cleaner than telemetry heads where a coating is applied to main housing 42. Coating 66 may be applied to interior shield 64 separate from the remaining assembly of telemetry head 40 so that there is little chance of contamination of other components within telemetry head 40. In contrast, in cases where coatings are applied to a main housing of a telemetry head, application of the coating often requires masking of other components within the telemetry head to avoid contamination when the coating was applied. An operator also has to be careful to avoid overspraying of a coating to the main housing to avoid contamination, whereas the application of coating 66 to shield 64 can be performed separate from assembly, so that there is little concern about overspraying.

In some examples, the material of coating 66 and any component onto which coating 66 is applied may not be recyclable, while components that have not been coated with a coating similar to coating 66 may still be recycled. Therefore, using a coating 66 that is only applied to an interior shield 64 that substantially surrounds at least a portion of antenna 46 allows for more of telemetry head 40 to be recyclable after telemetry head 40 has reached the end of its life. In one example, shield 64, e.g., upper shield 78 and lower shield 80, may be the only component of telemetry head 40 that is non-recyclable, in contrast to telemetry heads where a coating is applied to a main housing, where at least the main housing, and in some cases all of the telemetry head, may be non-recyclable.

As noted above, in some examples, where coating 66 is formed as an upper coating 82 on an upper shield 78 and a lower coating 84 on a lower shield 80, an electrical connection is for between upper coating 82 and lower coating 84. The smaller interior shield 64 described above provides for easier electrical connection around an entire edge of upper shield 78 and lower shield 80. In contrast, providing a shield coating on the main housing of a telemetry head generally only allows for electrical connection at one or more discrete positions around the hemispheres of the main housing. As noted above, electrical connection around substantially the entire edge of interior shield 64 may provide for better conduction of EMI-generated current in coating 66 away from telemetry antenna 46 and may provide for more reliable shielding.

As noted above, in some examples, telemetry antenna 46 transmits and/or receives inductive (magnetic) telemetry signals. The inductive telemetry signals may be conveyed as magnetic field signals. In such examples, telemetry antenna 46 may comprise a magnetic core 48. As further noted above, in some examples, coating 66 comprises a ferromagnetic material, such as nickel, that may be magnetically attracted to magnetic core 48. In some examples, the application of coating 66 to shield 64 may result in loose particles of coating 66, such as via flaking, friction from vibration, heating, etc. In some examples, due to the close proximity between coating 66 and magnetic core 48, magnetic core 48 may magnetically attract these loose particles so that they do not migrate to other parts of telemetry head 40 where they may have adverse affects, such as with electronics 58 or electrical connections between telemetry head 40 and cable 44. In addition to reducing or preventing contamination by loose particles of the material of coating 66, magnetic core 48 may also help to ensure that more of telemetry head 40 is recyclable. As noted above, the material of coating 66 is often non-recyclable such that any part of telemetry head 40 that comes into contact with loose particles of coating 66 may become non-recyclable. Magnetic core 48 tends to attract loose particles of coating 66 so that they do not come into contact with other components within telemetry head 40.

Figure 6:
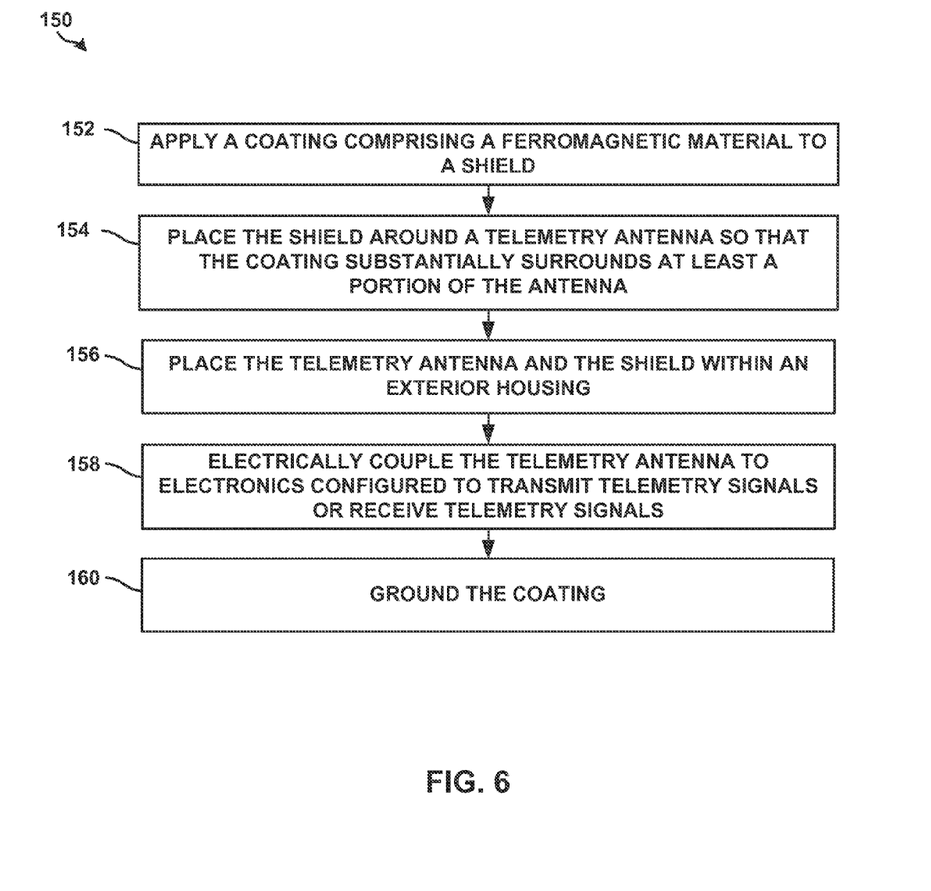
FIG. 6 is a flow chart illustrating an example method of making a telemetry head for communicating with an implantable medical device.

FIG. 6 is a flow chart illustrating an example method 150 of making a programmer system, such as a system comprising a telemetry head 40 and programmer 16 (FIG. 1). In one example method 150 comprises applying a coating 82, 84 comprising a ferromagnetic material to at least a portion of a surface 68, 72 of a shield 78, 80 (152), placing shield 78, 80 around at least a portion of a telemetry antenna 46 so that coating 82, 84 substantially surrounds at least the portion of telemetry antenna 46 (154). Coating 82, 84 is configured to shield at least the portion of telemetry antenna 46 from electromagnetic interference (EMI) fields while permitting telemetry signals to pass through coating 66. Method 150 further comprises placing telemetry antenna 46 and shield 78, 80 within an exterior housing 42 (156). In some examples, method 150 may further comprise electrically coupling telemetry antenna 46 to electronics configured to perform at least one of transmitting telemetry signals to telemetry antenna 46 or receiving telemetry signals from telemetry antenna 46 (158), wherein the electronics may be electronics 56 within a telemetry head 40 that comprises telemetry antenna 46, or the electronics may be comprised within a programmer 16. The example method 150 may also comprise grounding coating 82, 84 (160), for example by electrically coupling coating 82, 84 to a ground, such as a wiring board 60A.

In one example, applying coating 82, 84 (152) comprises applying coating 82 to at least a portion of a first major surface 68 of a shield 78 located on a first side 70 of telemetry antenna 46 and applying coating 84 to at least a portion of a second major surface 72 located on a second side 74 of telemetry antenna 46. Applying coating 82, 84 (152) may also comprise applying coating 82, 84 to substantially cover the entire first major surface 68 and substantially cover the entire second major surface 72.

In one example, applying coating 82, 84 (152) comprises applying a lower coating 84 to at least a portion of a surface 72, 94 of a lower shield 80 and applying an upper coating 92 to at least a portion of a surface 68, 92 of an upper shield 78, and the example method 150 further comprises electrically coupling lower coating 84 to upper coating 82. In one example, the method 150 further comprises mechanically coupling lower shield 80 to upper shield 78 via an interference fit between a lower mating surface 94 and an upper mating surface 92. In such an example, applying lower coating 84 to at least a portion of surface 72, 94 of lower shield 80 comprises applying lower coating 84 to lower mating surface 94, and applying upper coating 82 to at least a portion of surface 68, 92 of upper shield 78 comprises applying upper coating 82 to upper mating surface 92. In one example, the interference fit that provides for mechanical coupling is formed between upper mating surface 92 and lower mating surface 94 because upper mating surface 92 comprises a tapered angle θ and lower mating surface 94 comprises a corresponding mating tapered angle φ. In one example, upper portion tapered angle θ is approximately equal to lower portion tapered angle φ. In one example, electrically coupling lower coating 84 to upper coating 82 and mechanically coupling tower shield 80 and upper shield 78 are performed in a single step, wherein the interference fit between lower mating surface 94 and upper mating surface 92 provide for the electrical coupling between upper coating 82 and tower coating 84.

Various examples have been described. These and other examples are within the scope of the following claims.

The invention claimed is:

1. A telemetry head for communication with an implantable medical device, the telemetry head comprising:

a telemetry antenna; and a shield substantially surrounding at least a portion of the antenna, the shield having a coating comprising a ferromagnetic material applied to at least a portion of the shield, wherein the coating is applied to at least a portion of a first major surface of the shield located on a first side of the telemetry antenna and to at least a portion of a second major surface located on a second side of the telemetry antenna, wherein the coating is configured to shield at least the portion of the telemetry antenna from electromagnetic interference fields while permitting telemetry signals to pass through the coating.

2. The telemetry head of claim 1, wherein the telemetry antenna comprises a radio frequency antenna.

3. The telemetry head of claim 1, wherein the antenna comprises a magnetic core configured to transmit and receive inductive telemetry signals, wherein the shield surrounds at least a portion of the magnetic core.

4. The telemetry head of claim 1, wherein the ferromagnetic material of the coating comprises nickel.

5. The telemetry head of claim 1, wherein the ferromagnetic material of the coating comprises nickel and iron.

6. The telemetry head of claim 1, wherein the coating has a resistivity of between about 0.2 ohm per $cm^2$ and about 1 ohm per $cm^2$.

7. The telemetry head of claim 1, wherein the shield comprises a lower shield and an upper shield, the lower shield being mechanically coupled to the upper shield, wherein the coating comprises a lower coating applied to at least a portion of the lower shield and an upper coating applied to at least a portion of the upper shield, and wherein the lower coating is electrically coupled to the upper coating.

8. The telemetry head of claim 7, wherein the lower shield is mechanically coupled to the upper shield via an interference fit between a lower mating surface and an upper mating surface, wherein the lower coating is applied to the lower mating surface and the upper coating is applied to the upper mating surface, and wherein the lower coating is electrically coupled to the upper coating via the interference fit between the coated lower mating surface and the coated upper mating surface.

9. The telemetry head of claim 8, wherein the lower mating surface comprises a first taper comprising a first taper angle and the upper mating surface comprises a second taper comprising a second taper angle, wherein the first taper angle is between about 1 degree and about 3 degrees, and wherein the second taper angle is between about 1 degree and about 3 degrees.

10. The telemetry head of claim 9, wherein the first taper angle of the lower mating surface is approximately equal to the second taper angle of the upper mating surface.

11. The telemetry head of claim 1, further comprising electronics electrically coupled to the telemetry antenna, wherein the electronics are configured to transmit and receive telemetry signals via the telemetry antenna.

12. The telemetry head of claim 1, further comprising a housing enclosing the shield and the telemetry antenna.

13. A programmer for a medical device, the programmer comprising:

a telemetry antenna;

a shield substantially surrounding at least a portion of the antenna, wherein the shield comprises a lower shield and an upper shield, the lower shield being mechanically coupled to the upper shield, the shield having a coating comprising a ferromagnetic material comprising a lower coating applied to at least a portion of the lower shield and an upper coating applied to at least a portion of the upper shield, wherein the lower coating is electrically coupled to the upper coating, wherein the coating is configured to shield at least the portion of the telemetry antenna from electromagnetic interference fields while permitting telemetry signals to pass through the coating; and programmer electronics electrically coupled to the telemetry antenna, wherein the programmer electronics are configured to transmit and receive telemetry signals via the telemetry antenna.

14. The programmer of claim 13, wherein the telemetry antenna comprises a radio frequency antenna.

15. The programmer of claim 13, wherein the telemetry antenna comprises a magnetic core configured to transmit and receive inductive telemetry signals, wherein the shield surrounds at least a portion of the magnetic core.

16. The programmer of claim 13, wherein the ferromagnetic material of the coating comprises nickel.

17. The programmer of claim 13, wherein the coating has a resistivity of between about 0.2 ohm per cm2 and about 1 ohm per cm2.

18. The programmer of claim 13, wherein the lower shield is mechanically coupled to the upper shield via an interference fit between a lower mating surface and an upper mating surface, wherein the lower coating is applied to the lower mating surface and the upper coating is applied to the upper mating surface, wherein the lower coating is electrically coupled to the upper coating via the interference fit between the coated lower mating surface and the coated upper mating surface.

19. A system comprising:

an implantable medical device;

a telemetry head configured to communicate with the implantable medical device via telemetry signals, the telemetry head comprising;

a telemetry antenna; and a shield substantially surrounding at least a portion of the antenna, wherein the shield comprises a lower shield and an upper shield, the lower shield being mechanically coupled to the upper shield, the shield having a coating comprising a ferromagnetic material comprising a lower coating applied to at least a portion of the lower shield and an upper coating applied to at least a portion of the upper shield, wherein the lower coating is electrically coupled to the upper coating, wherein the coating is configured to shield at least the portion of the telemetry antenna from electromagnetic interference fields while permitting telemetry signals to pass through the coating; and a programmer electrically coupled to the telemetry head, the programmer comprising programmer electronics configured to transmit telemetry signals to the implantable medical device and to receive telemetry signals from the implantable medical device via the telemetry antenna.

20. The system of claim 19, wherein the telemetry antenna comprises a magnetic core to transmit and receive inductive telemetry signals, wherein the shield surrounds at least a portion of the magnetic core.

21. The system of claim 19, wherein the ferromagnetic material of the coating comprises nickel.

22. The system of claim 19, wherein the coating has a resistivity of between about 0.2 ohm per cm2 and about 1 ohm per cm2.

23. The system of claim 19, wherein the lower shield is mechanically coupled to the upper shield via an interference fit between a lower mating surface and an upper mating surface, wherein the lower coating is applied to the lower mating surface and the upper coating is applied to the upper mating surface, wherein the lower coating is electrically coupled to the upper coating via the interference fit between the coated lower mating surface and the coated upper mating surface.

24. A method comprising:
applying a coating comprising a ferromagnetic material to at least a portion of a shield, wherein the shield comprises a lower shield mechanically coupled to an upper shield, wherein applying the coating to at least the portion of the shield comprises applying a lower coating to at least a portion of the lower shield and applying an upper coating to at least a portion of the upper shield, the method further comprising electrically coupling the lower coating to the upper coating; placing the shield around at least a portion of a telemetry antenna so that the coating substantially surrounds at least the portion of the telemetry antenna, wherein the coating is configured to shield at least the portion of the telemetry antenna from electromagnetic interference fields while permitting telemetry signals to pass through the coating; and
placing the telemetry antenna and the shield within an exterior housing.

25. The method of claim 24, further comprising electrically coupling the telemetry antenna to electronics configured to transmit and receive telemetry signals via the telemetry antenna.

26. The method of claim 24, further comprising at least one of transmitting telemetry signals from the telemetry antenna to a medical device and receiving telemetry signals at the telemetry antenna from the medical device.

27. The method of claim 26, wherein the telemetry signals comprise inductive telemetry signals.

28. The method of claim 24, wherein the coating has a resistivity of between about 0.2 ohm per cm2 and about 1 ohm per cm2.

29. The method of claim 24, wherein the ferromagnetic material of the coating comprises nickel.

30. The method of claim 24, wherein the ferromagnetic material of the coating comprises nickel and iron.

31. The method of claim 24, further comprising mechanically coupling the lower shield to the upper shield via an interference fit between a lower mating surface and an upper mating surface, wherein applying the lower coating to at least the portion of the lower shield comprises applying the lower coating to the lower mating surface, and wherein applying the upper coating to at least the portion of the upper shield comprises applying the upper coating to the upper mating surface, wherein the lower coating is electrically coupled to the upper coating via the interference fit between the coated lower mating surface and the coated upper mating surface.

32. A telemetry head for communication with an implantable medical device, the telemetry head comprising:
a telemetry antenna; and
a shield substantially surrounding at least a portion of the antenna, wherein the shield comprises a lower shield and an upper shield, the lower shield being mechanically coupled to the upper shield, the shield having a coating comprising a ferromagnetic material comprising a lower coating applied to at least a portion of the lower shield and an upper coating applied to at least a portion of the upper shield, and wherein the lower coating is electrically coupled to the upper coating, wherein the coating is configured to shield at least the portion of the telemetry antenna from electromagnetic interference fields while permitting telemetry signals to pass through the coating.

* * * * *